United States Patent [19]
Kwasiborski et al.

[11] Patent Number: 6,033,708
[45] Date of Patent: Mar. 7, 2000

[54] METHOD FOR PRODUCING STERILE FILTERABLE LIPOSOME DISPERSION

[75] Inventors: Victoria Kwasiborski, Fall Church; Richard O. Cliff, Vienna, both of Va.; Alan S. Rudolph, Potomac, Md.

[73] Assignee: The United States of America as represented by the Secretary of the Navy, Washington, D.C.

[21] Appl. No.: 08/940,739

[22] Filed: Sep. 30, 1997

[51] Int. Cl.[7] ............................ A61K 9/127; A61K 9/133
[52] U.S. Cl. .............................. 426/450; 264/4.1; 264/4.3
[58] Field of Search .................................. 424/450, 1.21, 424/9.321, 9.51, 417; 264/4.1, 4.3; 436/829; 935/54

[56] References Cited

U.S. PATENT DOCUMENTS 4,229,360 10/1980 Schneider .................................. 260/403
4,746,516 5/1988 Moro ........................................ 424/450
5,340,587 8/1994 Mihalko .................................... 424/450
5,589,189 12/1996 Monynihan .

*Primary Examiner*—Gollamudi S. Kishore
*Attorney, Agent, or Firm*—Barry A. Edelberg

[57] ABSTRACT

The present invention relates to a composition and method of producing non-aggregating, filterable dispersion of liposome encapsulated agent or therapeutic of interest, specifically hemoglobin. A key step in the method of the present invention is the addition of a passivating protein prior to hydration of the liposomes with the agent of interest. The resulting dispersion is composed of unilamellar vesicles having a diameter of less than or equal to 0.2 microns.

5 Claims, No Drawings

METHOD FOR PRODUCING STERILE FILTERABLE LIPOSOME DISPERSION

BACKGROUND OF THE INVENTION

1. Field of the Invention

This invention relates to the field of blood substitutes, more specifically, a method for producing an oxygen-carrying encapsulated hemoglobin material that is sterile filterable.

2. Description of the Background Art

Liposome encapsulated hemoglobin, also known as a synthetic red blood cell, has been under development as a blood substitute for over a decade. For example, liposome encapsulated hemoglobin formulations and methods for making them are known in the art: U.S. Pat. Nos. 4,776,991 and 4,911,929 (Farmer), 4,532,130 (Djordjevich), 4,133,874 (Miller), and 5,589,189 (Moynihan). All documents cited herein are hereby incorporated by reference thereto. Liposomes are closed hollow spheres formed by a bilayer membrane of phospholipids. As liposomes are formed, water soluble molecules, such as hemoglobin, can be incorporated into the aqueous interior, and lipophilic molecules may be incorporated into the lipid bilayer. Liposomes may be either multilamellar, like an onion with liquid separating many lipid bilayers, or unilamellar, with a single bilayer surrounding an aqueous center. Unilamellar vesicles generally have a size less than 0.5 microns (um). Smaller unilamellar vesicles can be formed by a variety of techniques, such as applying a force sufficient to reduce the size of the liposomes and/or produce smaller unilamellar vesicles. Such force can be produced by a variety of methods, including homogenization, sonication or extrusion (through filters) of multilamellar vesicles. These methods result in dispersions of unilamellar vesicles having diameters of up to 0.2 um.

One important characteristic of a regulatory approved blood substitute or parenteral product is that it be sterile. Terminal sterile filtration is preferred to aseptic processing for the generation of a sterile parenteral product, and has been found to be the most effective in terms of processing and liposome stability. The best method for terminal sterile filtration is the sequential filtration of a dispersion of liposomes through a 0.45 and 0.22 um filtration system, and liposomes larger than 0.2 um, or aggregation of smaller liposomes will obstruct and clog this filter system as well as the ultrafiltration system employed to remove unentrapped components. The Farmer patents disclose the small scale filtration of a liposome encapsulated hemoglobin formulation dispersed in a hyperosmotic buffered saline solution through a 0.22 um filter. Similarly, Djordjevich discloses a laboratory process for filtering liposome encapsulated hemoglobin dispersed in a saline solution through a 0.22 micron filter for purposes of sterilization.

An important aspect of developing a liposome formulation, whether containing hemoglobin or a desired reagent or drug, is to achieve a unimodal or controlled particle size distribution of unilamellar liposomes having a median size less than 0.2 um. Controlling a particle size distribution provides not only for a sterile filterable product but it also provides other numerous processing and pharmacological benefits such as longer circulation time.

During the processing of liposome encapsulated hemoglobin, hemoglobin enters the liposome as expected, but is also associated with the outer surface of the liposome as evidenced by electron micrographs, and uv-visible spectroscopy. The surface-bound hemoglobin has been shown to be responsible for aggregation of the liposomes. The liposome aggregation has been the focus of much manufacturing efforts as the aggregate size is not amenable to 0.22 or 0.45 um sterile filtration, an essential feature of a large scale manufacturing process required for FDA approval.

Passivation of the surface of the liposome with a serum protein is known in the art (see Moynihan, U.S. Pat. No. 5,589,189) and has been used in an attempt to produce sterile filterable liposome dispersions. However, all of the samples processed with methods in the art display heterogeneous size distributions and sizes which do not allow 0.22 um filtration.

Therefore, the need exists for a method of producing liposome dispersions, specifically, liposome encapsulated hemoglobin that renders particle size distributions which allow sterile filtration.

SUMMARY OF THE INVENTION

The present invention satisfies the need described above. The present invention provides a method which results in a non-aggregating, filterable dispersion of liposomes with particle size distributions that are highly homogeneous and less than 0.2 um in diameter.

The method of the present invention is based the assumption that it is hemoglobin associated with the liposome surface which causes aggregation of the particles and prevents the ability to sterile filter. One key feature and significant difference between prior methods and the method of the present invention is the concentration and timing of the addition of the passivating protein. Addition of the appropriate concentration, preferably at 10 mg/ml, of passivating protein to the lipid before the lipid is exposed to hemoglobin reduces aggregate size, and enables sterile filtration through 0.22 or 0.45 micron filters. Only when the passivating protein is added to the lipid prior to the formation of a dry powder as is described in this application, followed by hydration with hemoglobin, or the agent of interest, does the process result in the formation of particles that can be sterile filtered.

Previous methods, including that described in the Moynihan patent (U.S. Pat. No. 5,589,189), add the passivating protein with the hemoglobin during the hydration step after the dry lipid powder is formed. Attempts to recreate the liposome dispersion according to Example 1 of the Moynihan patent produced a product described in Table 2 as Sample 2C of the present application and did not result in a nonaggregate, unimodal solution filterable through a 0.2 um filter.

The method described in this application provides exposure of the passivating protein to the liposome surface (and close association by drying or lyophilization) before the surface is then exposed to hemoglobin during the hydration step. This allows a reduction in aggregate formation due to hemoglobin associated with the surface of the liposome resulting in a unimodal, nonaggregate forming, sterile filterable liposome dispersion. The addition of sucrose in the present method also allows lyophilization of the particles.

The production of liposome encapsulated hemoglobin by the method described in this application provides reduced processing time over previous methods and results in a non-aggregating, unimodal, sterile filterable dispersion of liposome encapsulated hemoglobin which was previously not achievable.

Therefore, it is one object of the present invention to provide a method for the production of sterile filterable liposome dispersion, said method comprising the steps of:

(i) preparing a lipid powder in the presence of a passivating protein;

(ii) hydrating the lipid powder with an active therapeutic or an imaging agent to form a liposome dispersion containing said active therapeutic or imaging agent;

(iv) subjecting said dispersion to a force sufficient to reduce the median size of the liposomes to less than 0.2 um wherein the resulting liposomes are unilamellar;

(v) filtering the resulting liposomes through a filter having a size larger or equal to 0.22 um.

It is another object of the invention to provide a method for the production of sterile filterable liposome encapsulated hemoglobin, said method comprising the steps of:

(i) preparing a lipid powder in the presence of a passivating agent;

(ii) hydrating the lipid powder with hemoglobin to form a liposome dispersion containing said hemoglobin;

(iv) subjecting said dispersion to a force sufficient to reduce the median size of the liposomes to less than 0.2 um wherein the resulting liposomes are unilamellar;

(v) filtering the resulting liposomes through a filter passing particles having a size smaller than or equal to 0.2 microns.

It is another object of the present invention to provide a non-aggregating, filterable liposome dispersion of comprising liposomes with a median size smaller than or equal to 0.2 microns.

It is yet another object of the present invention to provide a non-aggregating, filterable dispersion of liposome encapsulated hemoglobin composition comprising liposomes containing hemoglobin wherein the liposomes have a median size smaller than or equal to 0.2 microns.

DETAILED DESCRIPTION OF THE PREFERRED EMBODIMENT(S)

In one embodiment, the present invention provides a method for producing a non-aggregating, filterable liposome dispersion comprising forming a dry powder or film containing a dispersion of multilamellar liposomes in the presence of a passivating protein.

The dry powder or film is formed containing a neutral lipid, cholesterol, and a negatively charged lipid. Alpha-tocopherol is a preferred ingredient commonly added in liposome formation as an antioxidant for free radical scavenging. Neutral lipids suitable for use include egg phosphatidylcholine, distearoyl phosphatidylcholine (DSPC), hydrogenated soy choline (HSPC), dimyristoylphosphatidylcholine (DMPC), hydrogenated egg phosphatidylcholine (HEPC), and dipalmitoylphosphatidylcholine. The preferred neutral lipids have carbon chain lengths from C16–C18. The preferred neutral lipid is DSPC. The negative lipids include hydrogenated soy phosphatidylglycerol (HSPG), hydrogenated egg phosphatidylglycerol (HEPG), distearyolphosphatidylglycerol (DSPG), dimyristoyl phosphatidylglycerol (DMPG), and dilaurylphosphatidylglycerol (DLPPG). The preferred negatively charged lipid is DMPG. The lipid film or powder is provided containing the formulation DSPC:DMPG:cholesterol:alpha-tocopherol in a molar ratio of 10:9:1:0.1. This general formula is taught in U.S. Pat. No. 4,911,929 to Farmer. In Farmer, it is disclosed that the neutral lipid is approximately 50% of the total lipid; the negatively charged lipid is approximately 10% of the total lipid and cholesterol is approximately 40% of the total lipid; and the alpha-tocopherol is approximately 2% of the total lipid. U.S. Pat. No. 5,589,189 to Moynihan discloses a similar lipid ratio of 10:9:1:0.4. The different ratio of alpha-tocopherol in the present invention (0.1 vs 0.4) is believed to be important to retard the oxidation of hemoglobin and enable lyophilization.

The lipids can be dissolved in an organic solvent such as chloroform, or a chloroform/methanol mixture; the preferred solvent is chloroform. The chloroform is removed from the lipids by evaporation on a Buchi Rotoevaporator at 65° C. The resulting lipid film is hydrated in buffer containing albumin and sucrose suitable for lyophilization. Other sugars such as lactose or trehalose, to name a few, may be used. Although the preferred embodiment of the invention is carried out having no phosphate buffer, the invention can be carried out using pH 7.4 phosphate buffer. An improvement in the electrostatic properties of the liposome is obtained when the dispersion is essentially free of ions (having essentially no ionic strength), and particularly being essentially free of phosphate ions, during the liposome forming procedure, or homogenization. The sucrose solution can be a concentration range from 5–15% weight to volume, preferably about 9% weight/volume.

The addition of albumin to the lipid must be made prior to hydration of the lipid film with the buffer and prior to the application of initial force. Preferably, the addition of albumin is during the hydration of the lipid film.

The dried lipid film (50–100 grams) is hydrated with a sterile filtered aqueous solution resulting in a lipid concentration of about 100 mg/ml. The aqueous solution contains about 5–15% wt/volume sucrose, preferably about 9%, and about 5–20 mg/ml human serum albumin, preferably about 10 mg/ml and hydration is for 30–60 minutes at 37–45 degrees centigrade. Upon hydration, the lipid solution is frozen, for example at −80° C., for up to about 24 hours in preparation for proper lyophilization so as to obviate thawing prior to drying in the freeze/dry cycle. Once frozen, the bulk sample is placed under lyophilization at frozen temperature initially with gradual heating up to room temperature after about 24 hours. The sample will become dry at 20 milliliter vacuum and room temperature in 2–3 days upon which hemoglobin hydration may proceed.

The lipid/albumin sample is then hydrated with hemoglobin in a saline solution, preferably phosphate free, in the range of about 10–25 g/dl. The lipid/albumin sample is hydrated with hemoglobin for 4–24 hrs, preferably, at 4–8° C., with mixing. Although human hemoglobin has been used for the present invention, other sources of hemoglobin including recombinant or transgenic hemoglobin or bovine/porcine hemoglobin may also be used. Additional hydration time optimizes the encapsulation efficiency and reduces liposome aggregation, which impedes processing. Hydration at a low temperature above freezing, such as 4° C., reduces the formation of methemoglobin. The combination of increased hydration time, and cooler temperatures allows for the reduction in processing time. The reduction in processing time, in turn, also helps to prevent the formation of methemoglobin Multilamellar liposome vesicles formed following hydration of the albumin lipid powder with hemoglobin are passed through a microfluidizer operating under an internal pressure of about 2000–2500 psi at subambient temperatures, preferably about 1–10° C. Microfluidization is carried out for 4–16 passes, preferably 4 passes. Additional albumin may be added during the application of force, in the concentration range of 5–20 mg/ml. Various globular plasma proteins may be used such as: albumin; immunoglobulin; alpha, beta, or gamma globulin; α-1 lipoprotein and mixtures thereof. The preferred protein is human serum albumin. The albumin concentration can vary between about 5–20 mg/ml, with a preferred concentration of about 10 mg/ml. The solution is further microfluidized under the same conditions for an additional 4–8 passes. The solution is ultrafiltered to removed the unencapsulated hemoglobin. The buffer exchange during ultrafiltration may be done with the solution containing about 2–4 mg/ml albumin to mimic physiological concentrations and about 5–10% w/v sucrose for lyophilization following the process. The solution is then passed through a series of filtration steps ending with the use of a filter that passes only particles having a size of about 0.2 μm in diameter (e.g., a 0.22 um filter) to provide for a sterile solution of liposome encapsulated hemoglobin. Separation of unencapsulated hemoglobin could proceed with various separation method such as centrifugation, dialysis, filtration, column chromatography followed by sterile filtration.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLE 1

Liposome encapsulated hemoglobin was prepared as follows.

Sample 1—(Lipid+HSA):

Distearoyl phosphatidylcholine, cholesterol dimyristoylphosphatidylglycerol and alpha-tocopherol in a molar ratio of 10:9:1:0.1 were dissolved in chloroform, and the chloroform evaporated. The sample was hydrated with a 9% sucrose and 10 mg/ml albumin solution and lyophilized. The sample was then hydrated with hemoglobin in solution in the range of 10–15 g/dl. Sample 1 was divided into aliquots as follows:

Sample 1A was microfluidized for 4 passes only;

Sample 1B was microfluidized for 4 passes, albumin was added, and the sample was microfluidized for a total of 8 passes;

Sample 1C was microfluidized for 4 passes, albumin was added, and the sample was microfluidized for a total of 16 passes.

Table 1 illustrates the difference in size for preparations as a result of the number of passes through the microfluidizer.

TABLE 1

Lipid + HSA

| Sample | Size (nm) | $mu^2$/gamma | Particle Size Distribution | |
|---|---|---|---|---|
| 1A | 220.5 | 0.26 | 229 nm | 100% |
| 1B | 217 | 0.37 | 182 nm | 99% |
| 1C | 197 | 0.35 | 171 nm | 100% |

EXAMPLE 2

Liposome encapsulated hemoglobin was prepared as follows.

Sample 2—(Lipid+HSA Post-Lyophilization):

Distearoyl phosphatidylcholine, cholesterol, dimyristoylphosphatidylglycerol and alpha-tocopherol in a molar ratio of 10:9:1:0.1 were dissolved in chloroform, and the chloroform evaporated. The sample was hydrated in buffer only and lyophilized. The sample was then hydrated with hemoglobin in solution in the range of 10–15 g/dl in a 9% sucrose, 10 mg/ml albumin solution.

Sample 2 was divided into aliquots as follows:

Sample 2A was microfluidized for 4 passes only;

Sample 2B was microfluidized for 4 passes, albumin was added, and the sample microfluidized for a total of 8 passes;

Sample 2C was microfluidized for 4 passes, albumin was added, and the sample microfluidized for a total of 16 passes. This sample is similar to that described in the Moynihan U.S. Pat. No. 5,589,189.

Table 2 illustrates the difference in size for preparations as a result of the number of passes through the microfluidizer.

TABLE 2

Lipid + HSA Post-lyophilization

| Sample | Size (nm) | $mu^2$/gamma | Particle Size Distribution | |
|---|---|---|---|---|
| 2A | 537.5 | 0.82 | 8070 nm | 61% |
| | | | 185 nm | 26% |
| | | | 1000 nm | 13% |
| 2B | 361 | 0.6 | 756 nm | 69% |
| | | | 151 nm | 31% |
| 2C | 242 | 0.39 | 284 nm | 100% |

EXAMPLE 3

Liposome encapsulated hemoglobin was prepared as follows.

Sample 3—(Lipid without HSA):

Distearoyl phosphatidylcholine, cholesterol, dimyristoylphosphatidylglycerol and alpha-tocopherol in a molar ratio of 10:9:1:0.1 were dissolved in chloroform, and the chloroform evaporated. The sample was hydrated in buffer only and lyophilized. The sample was then hydrated with hemoglobin in solution in the range of 10–15 g/dl. Sample 3 was divided into aliquots as follows:

Sample 3A was microfluidized for 4 passes only;

Sample 3B was microfluidized for 8 passes only;

Sample 3C was microfluidized for 16 passes.

TABLE 3

Lipid without HSA

| Sample | Size (nm) | $mu^2$/gamma | Particle Size Distribution | |
|---|---|---|---|---|
| 3A | 520 | 0.62 | 1040 nm | 78% |
| | | | 199 nm | 22% |
| | | | 25 nm | 0.50% |
| 3B | 400 | 0.61 | 2700 nm | 52% |
| | | | 289 nm | 47% |
| | | | 18 nm | 0.60% |
| 3C | 338 | 0.62 | 1020 nm | 69% |
| | | | 164 nm | 31% |

All of the samples processed with methods not described here display heterogenous size distributions and sizes which do not allow 0.22 um filtration. Only those samples in which the passivating protein is added to the lipid and a dry powder if formed, followed by hydration with hemoglobin result in the formation of particles that can be sterile filtered as shown in Table 1. Previous attempts by other methods, including the method described in the Moynihan U.S. Pat. No. 5,589,189, where the passivating protein is added with the hemoglobin during the hydration step after the dry lipid powder is formed did not produce sterile filterable liposomes (See Table 2, specifically, Sample 2C).

The method described in this disclosure results in the exposure of the passivating protein to the surface, and close association by drying, before the surface is then exposed to hemoglobin during hydration. The addition of sucrose in the process of the present invention also allows lyophilization of the particles after they are sterile.

The production of liposome encapsulated hemoglobin using the method of the present invention requires reduced processing time over previous methods and results in a non-aggregating, unimodal, sterile-filterable dispersion of liposome encapsulated hemoglobin which was previously not achievable.

What is claimed is:

1. A method for producing sterile filterable dispersion of liposomes having hemoglobin encapsulated therein, said method comprising the steps of:

(i) mixing cholesterol, a neutral lipid, a negatively charged lipid, and serum globular protein to form a lipid preparation;

(ii) hydrating said lipid preparation with hemoglobin to form a dispersion of liposomes containing said hemoglobin;

(iv) subjecting said dispersion to microfluidization at a pressure of 2000–2500 psi, said microfluidization reducing the median size of the liposomes to less than 0.2 um and producing, without sonication, a unimodal distribution of said liposomes, wherein the resulting liposomes are unilamellar;

(v) filtering the resulting liposomes through a filter passing particles having a size smaller than or equal to 0.2 microns.

2. The method of claim 1, wherein said serum globular protein is albumin.

3. The method of claim 1, wherein said dispersion is subjected to said microfluidization at said pressure for a total of 16 to 24 passes.

4. The method of claim 1, wherein said microfluidization forms a unimodal distribution of liposomes in which all of said liposomes are smaller than 0.2 $\mu$m.

5. The method of claim 4, wherein said dispersion is subjected to said microfluidization at said pressure for a total of 16 to 24 passes.

* * * * *